(12) United States Patent
Imakita et al.

(10) Patent No.: US 7,344,569 B2
(45) Date of Patent: Mar. 18, 2008

(54) CLOSED POSITION MAINTAINABLE SELECTOR VALVE, KNEE TORQUE DEVICE USING THE VALVE, AND ARTIFICIAL LEG

(75) Inventors: Toyohiko Imakita, Kobe (JP); Aritomo Fukui, Kobe (JP); Masahiko Okuda, Kobe (JP); Yoshiaki Nakaya, Kobe (JP)

(73) Assignee: Nabtesco Corporation, Tokyo (JP)

( * ) Notice: Subject to any disclaimer, the term of this patent is extended or adjusted under 35 U.S.C. 154(b) by 0 days.

(21) Appl. No.: 10/589,295

(22) PCT Filed: Sep. 9, 2004

(86) PCT No.: PCT/JP2004/013157

§ 371 (c)(1),
(2), (4) Date: Aug. 14, 2006

(87) PCT Pub. No.: WO2005/093305

PCT Pub. Date: Oct. 6, 2005

(65) Prior Publication Data

US 2007/0173953 A1 Jul. 26, 2007

(30) Foreign Application Priority Data

Mar. 29, 2004 (JP) ............................. 2004-097145

(51) Int. Cl.
*A61F 2/64* (2006.01)
*A61F 2/68* (2006.01)
*F16K 31/12* (2006.01)

(52) U.S. Cl. ........................... 623/43; 251/50; 251/52; 251/323

(58) Field of Classification Search .................. 623/39, 623/43–46; 251/48, 50, 52, 55, 323, 325
See application file for complete search history.

(56) References Cited

U.S. PATENT DOCUMENTS 2,790,180 A * 4/1957 Hauser ......................... 623/34

(Continued)

FOREIGN PATENT DOCUMENTS

JP 54-30528 10/1979

(Continued)

*Primary Examiner*—Bruce Snow
(74) *Attorney, Agent, or Firm*—Frommer Lawrence & Haug LLP; Ronald R. Santucci

(57) ABSTRACT

A selector valve capable of maintaining a closed position for a while even if an operating force to a valve element (80) is eliminated when the selector valve (10) is switched from a closed position (braking state) to an open position. The valve element (80) of the selector valve (10) receives an operating force from the outside and a returning force in the opposite direction of the operating force by a valve spring (90). Accordingly, the valve element (80) opens and closes the valve by making the first end (801) of the valve element (80) seat on/unseat from a valve seat (48) on the housing (20) side according to the presence or absence of the operating force. A first port (31) and a second port (32) on both sides of the valve seat (48) are connected or cut off from each other by the opening and closing. The valve element (80) is formed in a stepped structure, and receives a force based on a difference in pressure receiving area by the stepped structure which results from the pressure of hydraulic fluid. The force can maintain the closed position of the valve for a while.

9 Claims, 9 Drawing Sheets

U.S. PATENT DOCUMENTS 5,904,721 A * 5/1999 Henry et al. .................. 623/26
2005/0027370 A1 * 2/2005 Chen et al. .................. 623/26

FOREIGN PATENT DOCUMENTS

| JP | 05-337145 | 12/1993 |
| JP | 08-317944 | 12/1996 |
| JP | 2001-147635 | 5/2001 |
| JP | 2004-167106 | 6/2004 |

* cited by examiner

CLOSED POSITION MAINTAINABLE SELECTOR VALVE, KNEE TORQUE DEVICE USING THE VALVE, AND ARTIFICIAL LEG

This application is a 371 of PCT/JP2004/013157 filed on Sept. 9, 2004 and published on Oct. 6, 2005 under publication number WO 2005/093305 A1 and claims priority benefits of Japanese Patent Application No. 2004-097145 filed Mar. 29, 2004.

TECHNICAL FIELD

This invention relates to a selector valve for opening and closing a valve by an operating force from the outside, which selector valve is capable of maintaining a closed position for a while even if the operating force is eliminated, and it also relates to a knee torque device and an artificial leg using the selector valve.

BACKGROUND ART

A general hydraulic system (or hydraulic circuit) comprises a pressure source including a hydraulic pump for delivering a hydraulic fluid from a tank to the system, an actuator (for example, a hydraulic cylinder or hydraulic motor) for performing a required operation upon receipt of the supply of hydraulic fluid from the pressure source, and a control part (for example, a hydraulic control valve such as a selector valve) for controlling the pressure and flow rate of the hydraulic liquid in the system. Such a hydraulic system can be said as a system for performing an active operation by making good use of fluid energy of the hydraulic liquid.

In contrast, a hydraulic system relating to a human body frequently has no pressure source contrary to the general hydraulic system. As a device for assisting, for example, the movement by a joint such as a knee and an ankle), there is known a device for exerting a resisting force against the movement (for example, bending or flexing) of a human body. For example, Patent Document 1 shows an outfit or orthosis for the aged simulation and more particularly to a torque damper for exerting a resisting force against bending of the knee, Patent Document 2 shows a damper for a thigh prosthesis and more particularly to a unidirectional characteristic rotary damper for exerting a resisting force only when the knee is bent. Patent Document 3 shows a valve device, as a technique for braking the knee, for varying the restricting amount of a valve in accordance with the load of an artificial leg wearer loaded on the knee and generating a braking force (i.e., resisting force) in accordance with the restricting amount.

Patent Document 1: Japanese Patent Application Laid-Open No. 2001-147635
Patent Document 2: Japanese Patent Application Laid-Open No. H05-337145
Patent Document 3: Japanese Patent Application Laid-Open No. H08-317944

Such a hydraulic system for a human body is operated to convert a kinetic energy caused by a human body to a fluid energy in order to brake the former kinetic energy (movement of a human body). Therefore, the human body hydraulic system of this type is different from the general hydraulic system and has no pressure source. It performs a passive job. For the sake of convenience of explanation, in the description to follow, a specific application (application for flexibly bending the knee, in other words, for yielding function) in an artificial leg will be described. It should be noted, however, that the present invention relating to a hydraulic system for a human body has various applications such as, an outfit or orthosis for the aged simulation, an artificial leg and a rehabilitation apparatus (for example, an outfit for preventing bending of the knee at the time of rehabilitation).

DISCLOSURE OF THE INVENTION

Problem to be Solved by the Invention

When the hydraulic system for a human body brakes the movement of a human body, it is required for the system to control such that the braking action has a unidirectional characteristic or braking is effected when necessary. For example, speaking with respect to flexing/extending of the knee, it is required that braking is effected only when the knee is bent or flexed by putting the weight on the knee and no braking is effected when the knee is extended. To meet with this requirement, the hydraulic system comprises a selector valve for switching between a braking state where a braking force is generated and a non-braking state where the braking force is released. The valve element of the selector valve receives a controlling operating force at one end part and effects the opening/closing (that is, switching action) in accordance with presence or absence of the operating force. The switching control refers, in general, to the control for opening/closing the selector valve by motion of a single link of a link mechanism. However, the switching control is not limited to such mechanical control. For example, it is also possible that the moving state (for example, the walking state) of an objective human body is detected by a link of a link mechanism or an electrical sensor such as a strain gauge and the opening/closing control is electrically performed by a stepping motor based on the detection signal. As a technique suitable for mechanically detecting which part of the foot the load of a human body is loaded, there is already proposed a detecting method in which the human load loaded on the heel of the foot (a state where the valve is brought into a closed position and braking is effected) is discriminated from the load loaded on the toe (a state where the valve is brought into an open position and braking is released) utilizing a link mechanism which has an instantaneous center between the toe and the heal of the foot and serving the instantaneous center as a sensing point (Japanese Patent Application No. 2002-338626 filed on Nov. 21, 2002, corresponding to Japanese Patent Application Laid-Open No. 2004-167106 and also U.S. Publication No. U.S.-2005-0234562-A1).

A valve element of the selector valve to which an operating force is exerted from the outside is provided with a valve spring. The valve spring exerts a returning force to the valve element in a direction opposite to the operating force. Accordingly, the selector valve instantaneously switches the opening/closing state of the valve according to the presence or absence of the operating force. As a result of various experiments carried out, however, it became clear that this good responsibility adversely affects and many inconveniences result therefrom. For example, when a wearer of an artificial leg is walking on a downslope, an operating force exerted to the valve element of the selector valve is, in some case, abruptly released while the time the braking effect is acting on the knee. This occurs from a fact that the presence or absence of the operating force is based on a delicate detecting result according to the walking state of the artificial leg wearer. This occurrence is difficult to avoid completely taking into consideration that human walking has an individual character or the walking style itself can be changed. At any rate, since there is a worry of bending of the knee when the braking force is abruptly released, some safety measures are demanded.

It is, therefore, an object of the present invention to provide a technique capable of maintaining a closed position for a while even if an operating force to be exerted to a valve element is eliminated when a selector valve is switched from a closed position (braking state) to an open position.

Another object of the present invention is to provide a technique capable of maintaining a closed position of a valve element under the effect of pressure of a hydraulic liquid surrounding a valve element when the pressure is a predetermined value or more.

Other objects of the present invention will become manifest from the description to be made hereinafter.

Means for Solving the Problem

The subject matter of the present invention is a specific selector valve for performing the opening/closing of a valve by an operating force from the outside. A valve element of this selector valve receives not only an operating force from the outside but also a returning force (spring force in a direction opposite to the operating force) by a valve spring. Accordingly, the valve element is constituted such that a first end of the valve element is made to seat on/unseat from a valve seat according to the presence or absence of the operating force so that the valve is opened or closed. By the opening or closing of the valve, a first port and a second port, which are located with the valve seat disposed therebetween, are communicated/discommunicated from each other. According to the teaching of the present invention, a closed position can be maintained for a while even if an operating force from the outside is eliminated. Additional constitutions relate to the following features.

(A) The valve element is formed in a stepped structure, and receives a force based on a difference in pressure receiving area by the stepped structure which results from the pressure of hydraulic fluid flowing through the first and second ports, and (B) a seating state of the valve element seated on the valve seat is maintainable by force based on a difference in pressure receiving area by the stepped structure of the valve element when the first end of the valve element is seated on the valve seat on the housing side.

The valve element may be comprised of a single component part or a plurality of component parts movable with respect to each other. In case the valve element is comprised of a single component part, the valve element includes an enlarged-diameter part on the side facing the first port and a reduced-diameter part near an opening of a cylinder hole. The valve element further includes an internal path for communicating the first port and the outer periphery of the reduced-diameter part with each other through an inner peripheral side of a part seated on the valve seat. The enlarged-diameter part and the reduced-diameter part of the valve element of course have a stepped structure so that a force is generated based on a difference in pressure receiving area. In case the valve element is comprised of a plurality of component parts, the valve element includes, for example, an outer piston having an internal hole along the axial direction and an inner piston movably fitted to the internal hole of the outer piston. In correspondence therewith, the valve spring includes a main spring for exerting a returning force to the outer piston and a secondary spring for exerting a returning force to the inner piston. In case the valve element is comprised of a plurality of component parts as mentioned above, one of the plural component parts may have a stepped structure. In view of easiness of communication of a hydraulic fluid with the stepped part, the inner component part (inner piston) is preferably provided with a stepped structure. In that case, since the selector valve exhibits three states, i.e., a fully closed state, a half-open state and fully open state, the valve maintains a half-open restricting state for a while instead of being switched to the fully open state when the valve is switched from the fully closed state to the fully open state. This "half-open restricting state" refers to the "closed position" of the valve. The same is applicable to the "fully closed state".

Such a selector valve can effectively be applied to, for example, a knee torque device for exerting a resisting force to the flexing of the knee. The knee torque device basically comprises, for example, a first chamber into which a hydraulic liquid is entered when the knee is extended, a second chamber into which a hydraulic liquid is entered when the knee is flexed, a path for communicating the second chamber and the first chamber with each other, a restrictor located on the path between the first chamber and the second chamber and exerting a resisting force to the flexing of the knee utilizing the flow of the hydraulic liquid passing through the restrictor, a check valve connected to the restrictor in parallel on the path, prohibiting the flow from the first chamber to the second chamber and allowing the flow in the reverse direction, and a selector valve connected to the check valve and the restrictor in parallel on the path. As the last-mentioned selector valve, a valve having the respective features of (A) and (B) is used. By doing so, the knee can be prevented from being bent abruptly while effectively utilizing such a feature as being capable of maintaining a closed position for a while even if an operating force from the outside is eliminated.

The restrictor in the knee torque device exerts a resistance to the flow of a hydraulic liquid passing therethrough, so that the knee can be flexed flexibly. The flexing resistance has such a magnitude, for example, 40 to 100 Nm, that a person using the knee torque device (an artificial leg wearer, a person under rehabilitation and thus wearing no artificial leg, or the like) can flex the knee slowly by loading his/her own load (weight) on the knee. As the restrictor, a variable restrictor or a stationary restrictor may be used. From a view point that the amount of restriction is made adjustable in accordance with the wearer's characteristic and preference, a variable restrictor is preferable. The check valve connected to the restrictor in parallel is arranged in order to generate a resisting force (braking force) only when the knee is flexed, in other words, in order not to generate a resisting force by the restrictor when the knee is extended. As the check valve, a valve having a simple structure serving a ball or a popett as a valve element.

The knee torque device includes a means for defining two chambers into and out of which a hydraulic liquid flows. As the means for defining two chambers, a piston type including a reciprocally movable piston or a rotary type including an oscillating vane may be applied. From a view point of making the knee circumference small, the rotary type is preferable. U.S. Pat. No. 5,704,945 (corresponding to Japanese Patent Application Laid-Open No. H08-317944), U.S. Pat. No. 2,667,644 and some others. disclose the rotary type, while U.S. Pat. No. 2,530,286, U.S. Pat. No. 2,568,053 and some others disclose the piston type.

The selector valve in the knee torque device may be set to any of the normally open or normally closed. From a view point of reliably preventing the bending of the knee by reliably effecting the braking operation at normal time, the normally closed is preferable. The artificial leg sometimes includes an air cylinder device for assisting the flexing and extending of the knee in a swing phase in addition to a device for obtaining a yielding function in a stance phase. In a case of such an artificial leg, from a view point not to disturb the swing phase controlling by the air cylinder device, the normally open is superior. In a selector valve of the normally open type, the open position in a free state can be set as nearer as possible to the closed position. The valve can also be set to the normally open but at the same time, to the intermediate (in a sense, normally neutral) between the normally open and the normally closed. In case the valve is set to the normally neutral, the valve can be switched from the open position to the closed position with a small load and thus, the braking force can easily be obtained. Also, the state of an open position or closed position can be maintained or in a sense, memorized by mechanical friction of a member (for example, a link constituting a link mechanism) for exerting an operating force in a free state.

The characteristic of the selector valve according to the present invention, namely, such a characteristic that a closed position can be maintained for a while even if an operating force to the valve element is eliminated, will be described more specifically. In the selector valve according to the present invention, since the valve element includes a stepped structure part, a difference in pressure receiving area occurs at the part which is subjected to pressure of the hydraulic liquid and a force is generated in a directing for closing the valve based on a difference in pressure receiving area. The force based on a difference in pressure receiving area is determined by the largeness of difference in pressure receiving area resulting from the stepped structure and the magnitude of pressure of the hydraulic liquid. The pressure of the hydraulic liquid around the valve element is generated when a load is loaded in a flexing direction of the knee (i.e., generated as a braking force) and released when the load is removed. Accordingly, taking into consideration of the magnitude of the pressure generated, setting can be made such that the force based on a difference in pressure receiving area and the spring force of the valve spring for exerting a returning force to the valve element are well balanced. By doing so, even if an operating force to the valve element is abruptly eliminated when a predetermined braking pressure is generated within the valve in a closed position, the valve can be maintained in a closed position for a while during which the pressure of the hydraulic liquid in the valve is lowered. If an arrangement is made such that a restricting action is generated in the midway of the internal path communicated with the stepped part of the valve element, the time for lowering the pressure of the hydraulic liquid around the stepped part can slightly be delayed. In order to meet with difference in walking style which is different by individuals or in order to fit to the walking feeling which is different by individuals, such a restricting action as just mentioned can also be good used.

Figure 1:
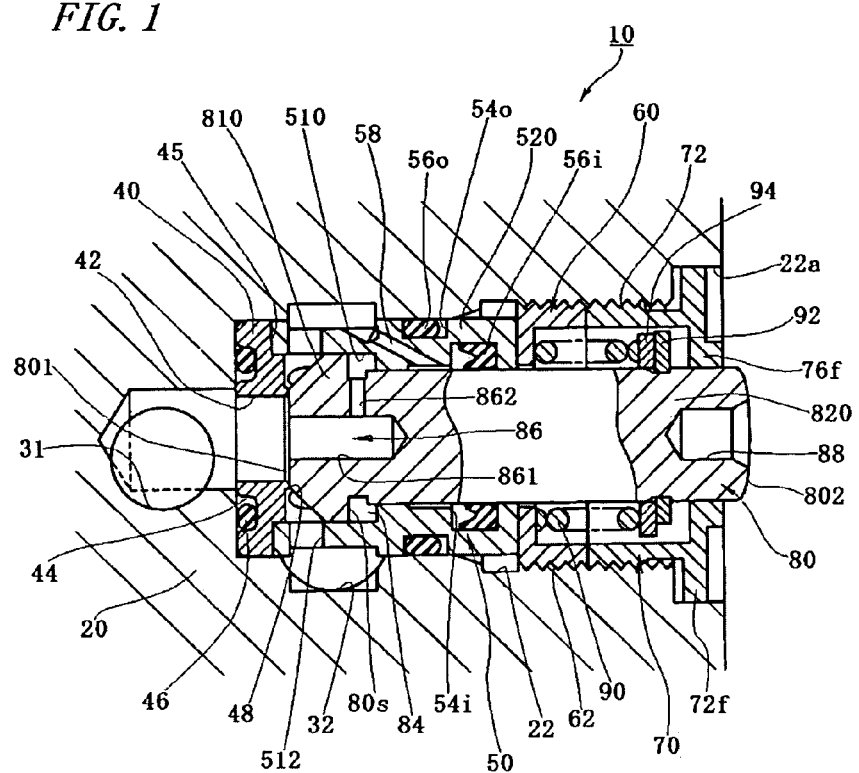
FIG. 1 is a sectional view showing a first embodiment of a selector valve according to the present invention.

DESCRIPTION OF REFERENCE NUMERAL 10, 102, 103, 104, 105 . . . selector valve
20 . . . housing
22 . . . cylinder hole
31 . . . first port
32 . . . second port
40 . . . valve seat member
48 . . . valve seat
50 . . . holder
60 . . . screw ring
64 . . . spacer
68 . . . free piston
684 . . . ball valve element
686 . . . hydraulic liquid chamber
70 . . . cover ring
80 . . . valve element
801 . . . first end
802 . . . second end
810 . . . enlarged-diameter part
820 . . . reduced-diameter part
830 . . . inner piston
84 . . . small chamber
86 . . . internal path
90 . . . valve spring (main spring)
1000 . . . knee torque device
7000 . . . air-cylinder device

BEST MODE FOR CARRYING OUT THE INVENTION

First Embodiment of Selector Valve

FIG. 1 is a sectional view showing a first embodiment of a selector valve. The selector valve 10 is placed within a cylinder hole 22 formed in a housing 20. The cylinder hole 22 is a blind hole extending in an axial direction. There is an opening 22a at one surface of the housing 20. At the innermost of the cylinder hole 22, there is a first port 31

There is a second port 32 on the side near the opening 22*a* from the first port 31 when viewed in the axial direction. The selector valve 10 is a control valve for communicating/cutting off the first port 31 side and the second port 32 side by being opened/closed. At the depth of the cylinder hole 22, there is a valve seat member 40 between the first port 31 and the second port 32. The valve seat member 40 has a through-hole 42 passing through the center thereof. One opening of the through-hole 42 is faced with the first port 31, while the other opening thereof is faced with the second port 32. The valve seat member 40 is provided at one surface on the housing 20 side with a seal ring attaching groove 44 which retains an O-ring 46. The O-ring 46 seals between the housing 20 side and the valve seat member 40 side. When the selector valve 10 is closed, the O-ring 46 closes the side which is in communication with the first port 31.

The valve seat member 40 has a ring-like valve seat 48 at the peripheral part of the other opening of the through-hole 42. It is preferable that the valve seat 48 is convexly bulged and has favorable seat characteristics. The valve seat member 40 is provided at the outer periphery of the valve seat 48 with a joint groove 45 into which one end of a holder 50 is received. The holder 50 is cylindrical. The diameter on the inner peripheral side of the cylindrical holder 50 is enlarged on the side jointed to the valve seat member 40 and reduced on the side near the opening 22*a* of the cylinder hole 22. There are a plurality (for example, eight) of round holes 512 equally spacedly arranged in a peripheral direction on an enlarged-diameter hole part of the holder 50. Through those round holes 512, the inner and outer peripheries of the enlarged-diameter hole part 510 are communicated with each other. The holder 50 is provided at a reduced-diameter hole part 520 with seal ring attaching grooves 54*i*, 54*o* which are formed in inner and outer peripheries, respectively. The inner peripheral seal ring attaching groove 54*i* retains a cup seal 56*i*, while the outer peripheral seal ring attaching groove 54*o* retains an O-ring 56*o*. A valve element (as later described) is engaged with the inner periphery of the holder 50 which is contacted with the valve element almost in a liquid tight manner. Owing to this arrangement, a closed space is defined in the inner peripheral part of the reduced-diameter hole part 520 of the holder 50. In order to release the closed space, the holder 50 has a slantwise path 58 for communicating the outer periphery of the enlarged-diameter hole part 510 and the inner periphery of the reduced-diameter hole part 520.

The holder 50 is supported by a screw ring 60 and a cover ring 70. Both the rings 60, 70 are component parts which have screw parts 62, 72, respectively, on the outer periphery. Those screw parts 62, 72 are threadingly engaged with the screw part of the cylinder hole 22, thereby being fixed to the housing 20. The screw parts 62, 72 positionally retain other component parts within the cylinder hole 22. The cover ring 70 is provided on the opening 22*a* side of the cylinder hole 22 with an outward flange part 72*f* and an inward flange part 76*f*. The outward flange 72*f* serves to support the cover ring 70 with respect to the housing 20 in a stable manner, while the inward flange 76*f* serves to guide a valve element (as later described).

The cylinder hole 22 is provided at the inner periphery with a plurality of guide parts for guiding the valve element. The respective parts of the enlarged-diameter hole part 510 and the reduced-diameter hole part 520 of the holder 50, as well as the inward flange 76*f* of the cover ring 70, serve as such guide parts, respectively. The valve element 80 is of a stepped structure. The stepped valve element 80 comprises an enlarged-diameter part 810 fitted to the enlarged-diameter hole part 510 of the holder 50, and a reduced-diameter part 820 connected the enlarged-diameter part 810 through a stepped part 80*s*. A first end 801 of the valve element 80 brought into the cylinder hole 22, i.e., a front face of the enlarged-diameter part 810 of the valve element 80 is faced with the valve seat 48 of the valve seat member 40. Owing to this arrangement, the valve element 80 is moved in the axial direction guided by the respective guide parts, thereby the first end 801 of the valve element 80 is seated and unseated from the valve seat 48. The diameter of the first end 801 of the valve element 80 is only slightly larger than the diameter of the valve seat 48. Owing to this arrangement, when the first end 801 of the valve seat 80 is unseated from the valve seat 48, the first port 31 side and the second port 32 side are resistance-freely and smoothly communicated with each other through the round holes 512.

The stepped valve element 80, together with the holder 50, defines a ring-like small chamber 84 at the outer peripheral part of the reduced-diameter part 820 adjacent to the stepped part 80*s* of the valve element 80. This small chamber 84 is important in a sense that a force based on a difference in pressure receiving area between the enlarged-diameter part 810 and the reduced-diameter part 820 which results from the pressure of hydraulic fluid is acted on the valve element 80. To this end, the valve element 80 has an internal path 86 for communicating the small chamber 84 and the first port 31 side with each other. The internal path 56 comprises a first hole 861 opening to the first end 801 of the valve element 80 and extending from the enlarged-diameter part 810 to a part of the reduced-diameter part 820, and a second hole 862 extending in the axial direction within the reduced-diameter-part 820 adjacent to the stepped part 80*s* and adapted to communicate the first hole 861 and the small chamber 84 with each other.

The valve element 80 is subjected to force caused by a valve spring 90 that is a coiled spring. A first spring retainer, which is formed by a C-type stop ring 92 and a flat washer 94, is disposed at the reduced-diameter part 820 of the valve element 80 located at the inner periphery of the cover ring 70. One end of the valve spring 90 is abutted with the flat washer 94 which is supported by the stop ring 92, while the other end is abutted with an inward flange part of the screw ring 60. Accordingly, the spring force of the valve spring 90 acts in a direction separating the first end 810 of the valve element 80 from the valve seat 48. A second end 802, i.e., the end of the reduced-diameter part 820 one the opposite side of the enlarged-diameter part 810, of the valve element 80 is passed through the cover ring 70 located at the opening 22*a* part of the cylinder hole 22 and protruded from one surface of the housing 20. The protruded second end 802 is provided at a center thereof with a blind hole 88 which serves as a joining point for joining a member (for example, a link) for exerting an operating force from the outside to the valve element 80. A damping member such as, for example, a rubber may be disposed at the joining point. The blind hole 88 also serves as means for reducing the weight of the valve element 80 by reducing the capacity of the valve element 80 that is made of metal.

This selector valve 10 can change the spring force of the valve spring 90 by properly selecting the flat washer 94. In this way, the selector valve 10 can be set to be a normally open state or normally closed state. When the selector valve 10 is in the normally open state, the force caused by the valve spring 90 is set to be larger than the operating force exerted to the second end 802 of the valve element 80 from the outside, and when the selector valve 10 is in the normally closed state, the force caused by the valve spring 90 is set to be smaller than the operating force exerted to the second end 802 of the valve element 80 from the outside. In any of the setting, the selector valve 10 can achieve the yielding function by increasing the pressure (internal pressure) on the first port 31 side in accordance with the movement of accompanying with, for example, the flexing of the knee when the first end 801 of the valve element 80 is seated on the valve seat 48. Even if the operating force from the outside should be suddenly eliminated when a predetermined pressure is generated on the first port 31 side (when the yielding function is effective), the selector valve 10 would keep the closed position for a while because the force based on a difference in pressure receiving area of the valve element 80 which results from the pressure on the first port 31 side overcomes the spring force of the valve spring 90.

Second Embodiment of Selector Valve

Figure 2:
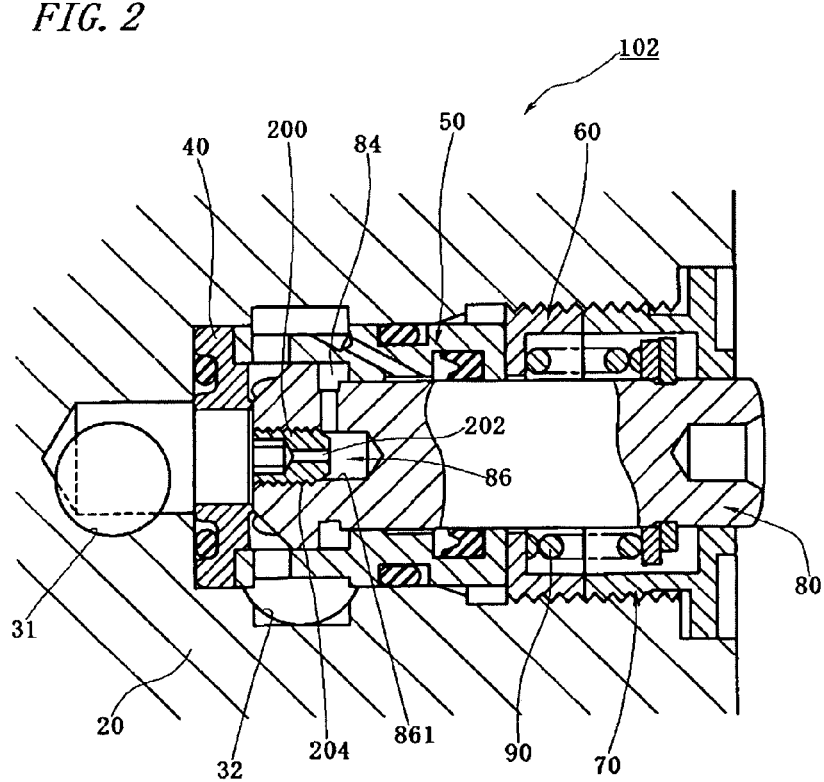
FIG. 2 is a sectional view showing a second embodiment of a selector valve according to the present invention.

FIG. 2 is a sectional view showing a second embodiment of a selector valve. This second embodiment is an example obtained by modifying a part of the first embodiment of FIG. 1. A selector valve 102 as the second embodiment additionally includes a restricting member 200 placed at an internal path 86 of the selector valve 10 of the first embodiment. The restricting member 200 includes, in addition to a restricting path 202 disposed at a central part, an attaching screw part 204 disposed at the outer periphery. Accordingly, by threading a screw fittable to the attaching screw part 204 of the restricting member 200 in a first hole 861 of the central part of the valve element 80, the restricting member 200 can be fitted into the first hole 861 by threading engagement. In some case, the restricting member 200 may be removed so that the selector valve 102 may have the same form as the selector valve 10 of the first embodiment. When the pressure generated on the first port 31 side is lowered, the selector valve 102 having the restricting member 200 releases the pressure in the small chamber 84 through the restricting path 202. Under the restricting action made by the restricting member 200, the time for maintaining the selector valve 102 in the closed position can be controlled, thereby enabling to avoid the bending of the knee effectively.

Selector Valve of Third Embodiment

Figure 3:
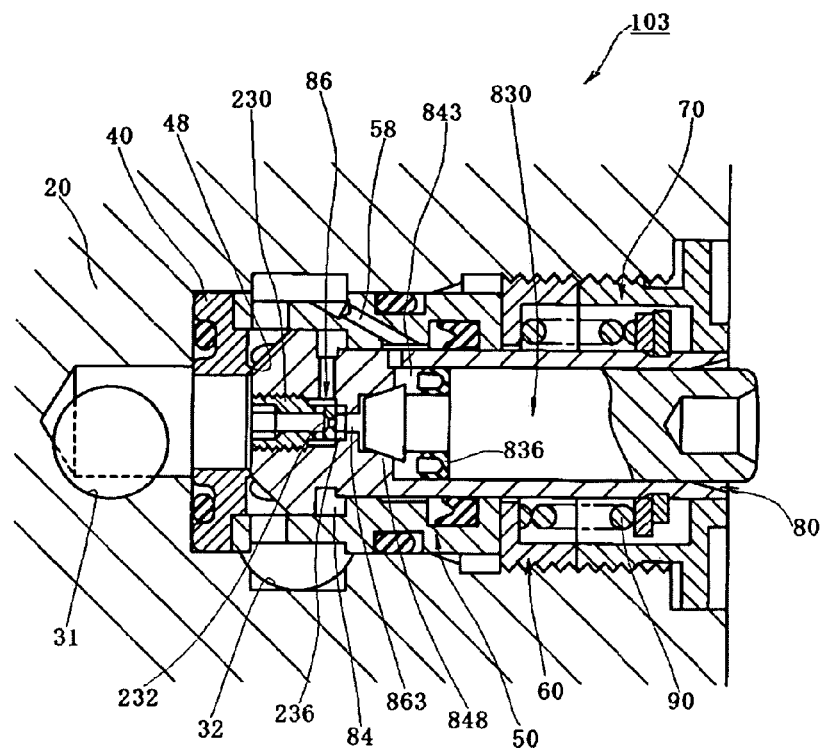
FIG. 3 is a sectional view showing a third embodiment of a selector valve according to the present invention.

FIG. 3 is a sectional view showing a third embodiment of a selector valve. This third embodiment is an example obtained by further modifying the selector valve 102 of the second embodiment. A selector valve 103 as the third embodiment includes, in addition to a restricting member 230 placed at the internal path 86, an inner piston 830 disposed within the valve element 80. The inner piston 830 holds a seal ring 836 at a front end part thereof, thereby defining an internal chamber 843 within the valve element 80. The inner piston 830 cuts off or communicates the third hole 863 and the internal chamber 843 with each other by making the front end part seat on/unseat from an internal valve seat 848 of the valve element 80. The restricting path 232 of the restricting member 230 is communicated with the internal chamber 843 through a gasket 236 and a third hole 863. An operating force to be exerted from the outside to the valve element 80 is transmitted to the valve element 80 through the inner piston 830. When the operating force from the outside is eliminated, the inner piston 830 is subjected to pressure from the third hole 863 and its front end part is unseated from the internal valve seat 848. This causes the pressure in the small chamber 84 to flow gradually into the internal chamber 843 through the restricting path 232 and release the pressure toward the second port 32 side through a diagonal path 58. As a result, the pressure on the first port 31 side is gradually lowered. When the pressure is lowered to a predetermined valve or lower, the first end 801 of the valve element 80 is returned to a position away from the valve seat 48 under the effect of the valve spring 90.

Fourth Embodiment of Selector Valve

Figure 4:
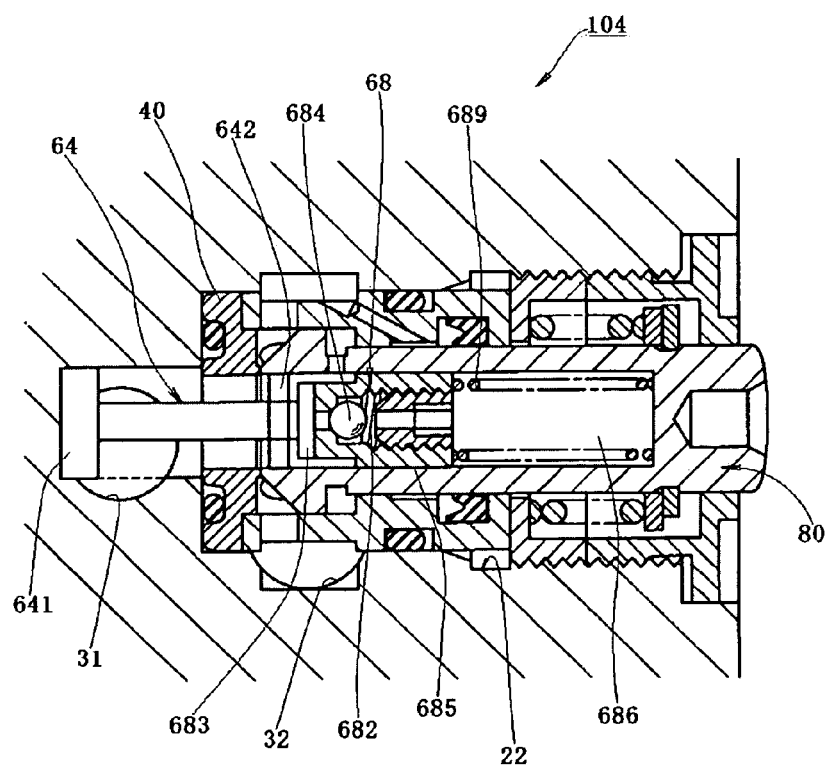
FIG. 4 is a sectional view showing a fourth embodiment of a selector valve according to the present invention.
Figure 5A:
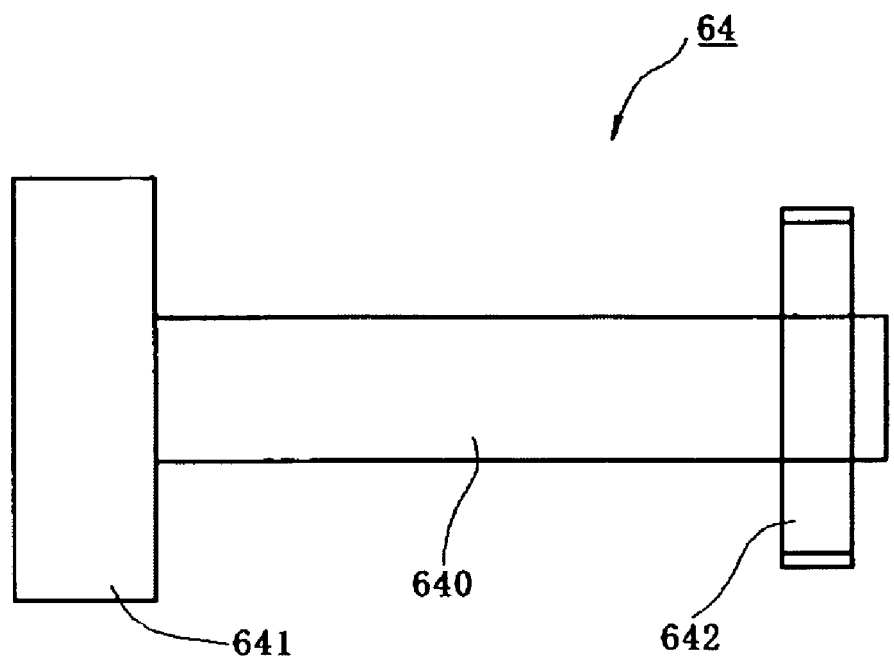
FIG. 5A is a front view showing a spacer of the selector valve of the fourth embodiment.
Figure 5B:
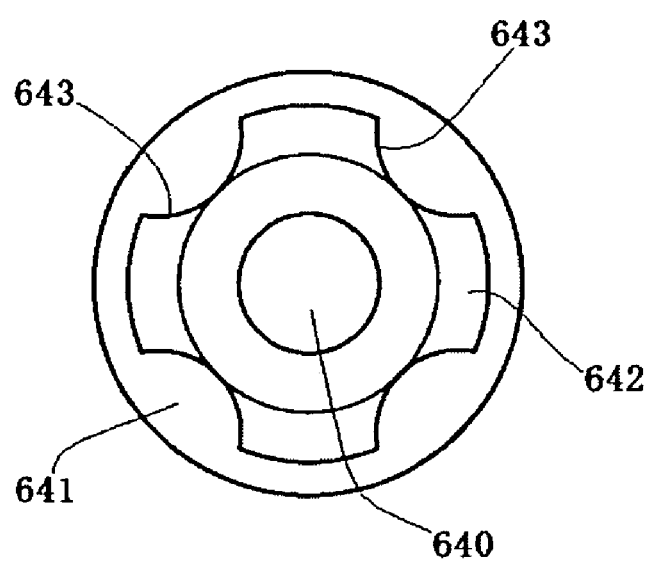
FIG. 5B is a side view showing the spacer of the selector valve of the fourth embodiment.

FIG. 4 is a sectional view showing a fourth embodiment of a selector valve. The selector valve 104 of this fourth embodiment has, in addition to the feature that it can maintain the closed position for a while as in other embodiments, such an additional feature that the difficulty encountered when the normally closed position is set, i.e., the difficulty that due to the normally closed position, a flexing resistance occurs in a swing phase, can be eased. The selector valve 104 comprises a spacer 64 passing through the valve seat member 40 and a free piston 68 disposed within the valve element 80. FIGS. 5A and 5B are illustration showing the construction of the spacer 64. The spacer 64 is provided at the opposite end parts of a rod 640 with support parts 641, 642, respectively. The respective support parts 641, 642 are fitted to holes at the midways of the respective paths and support the spacer 64 itself. A plurality of groove paths 643 are formed in the outer periphery of the support part 642 fitted to the hole of the valve element 80 Through those groove paths 643, the small chamber 84 side and the first port 31 side are freely communicated with each other. The spacer 64 functions as a stopper against the free piston 68.

Figure 6A:
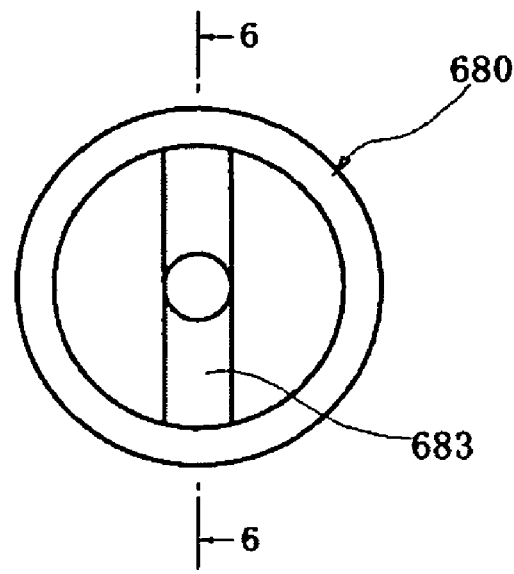
FIG. 6A is a side view showing a piston main body of a free piston of the selector valve of the fourth embodiment.
Figure 6B:
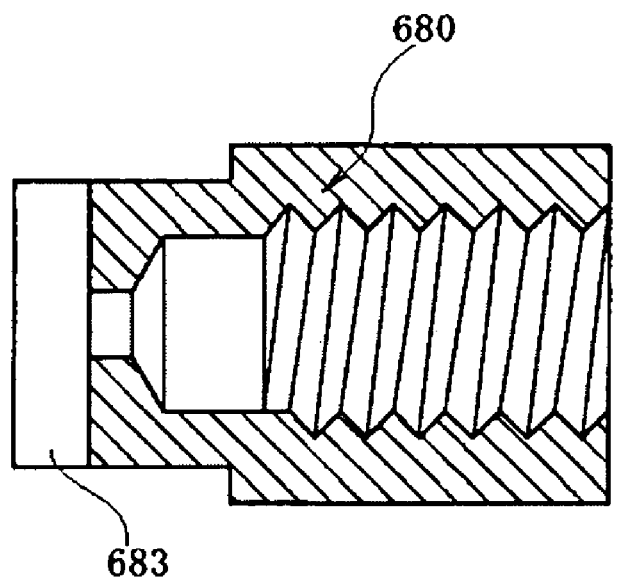
FIG. 6B is a sectional view taken on line 6-6 of FIG. 6A

FIGS. 6A and 6B show a piston main body 680 of the free piston 68. The piston main body 680 has a valve chest 682 defined therein. A ball valve element 684 is received in the valve chest 80. The free piston 68 defines an hydraulic liquid chamber 686 within the valve element 80. A coiled spring 689 is disposed within the hydraulic liquid chamber 686. This coiled spring 689 pushes the free piston 68 so that a front end of the piston main body 680 is abutted with the spacer 64 side. As shown in FIGS. 6A and 6B, since there is a provision of the radially crossing groove path 683 at the front end of the piston main body 680, the flow of the hydraulic liquid is not jeopardized by abutment of the piston main body 680 with the spacer 64. As paths extending from the hydraulic liquid chamber 686 to the spacer 64 side, there are a path formed within the piston main body 680 and a restricting path 685 formed at the outer periphery of the piston main body 680. The ball valve element 684 placed within the piston main body 680 prohibits the hydraulic liquid in the hydraulic liquid chamber 686 from flowing toward the first port 31 side. To this end, when the normally closed selector valve 104 is returned from the open position to the closed position, a restricting action by the restricting path 685 is effectively acted on the hydraulic liquid which is caused to flow from the hydraulic liquid chamber 686 to the first port 31 side under the effect of a check valve exhibited by the ball valve element 684. Accordingly, the selector valve 104, which would otherwise be returned to the closed position, can be maintained in the open position for a while by the restricting action made by the restricting path 685. This acts in such a manner that the flexing resistance is eliminated in the swing phase.

Fifth Embodiment of Selector Valve

Figure 7:
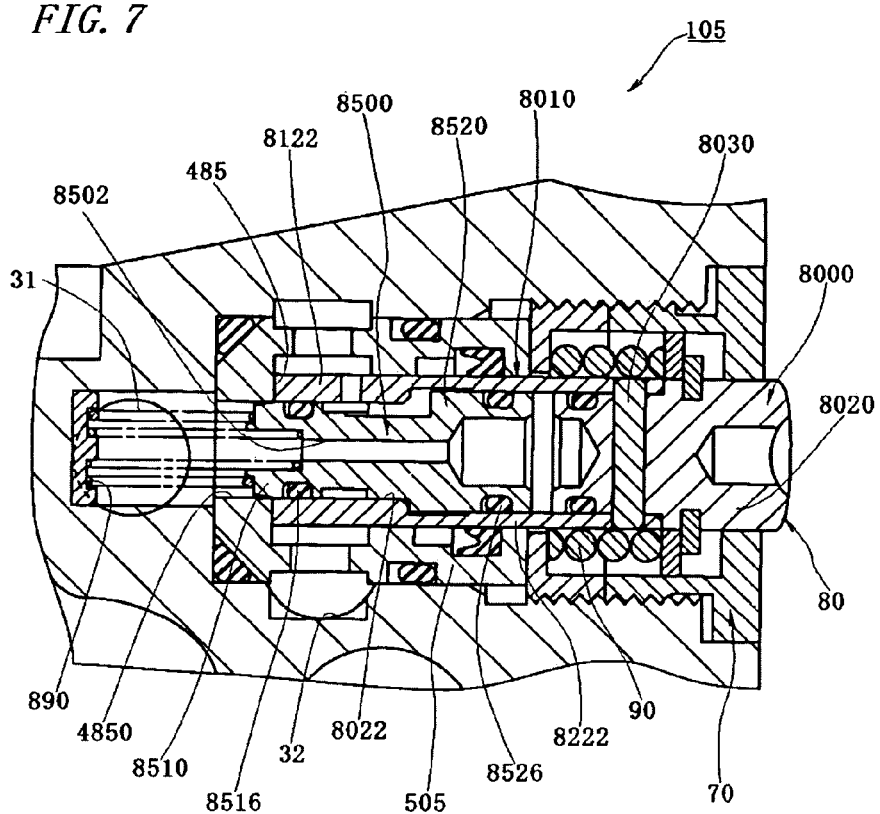
FIG. 7 is a sectional view showing a fully closed state of a fifth embodiment of a selector valve according to the present invention.
Figure 8:
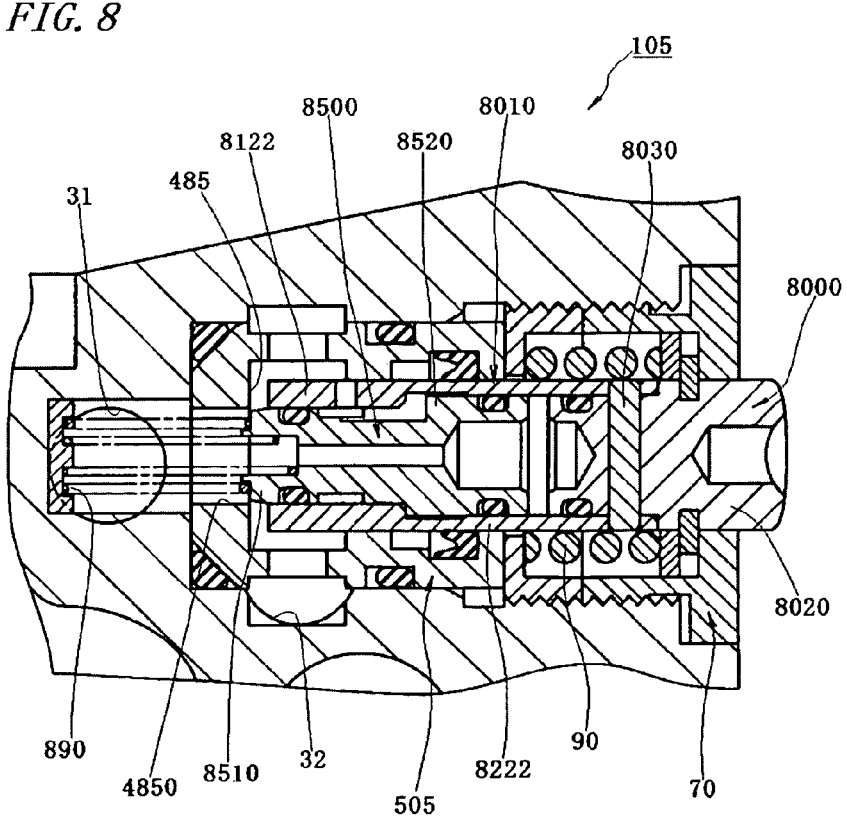
FIG. 8 is a sectional view showing a half-open state of the fifth embodiment of the selector valve according to the present invention.
Figure 9:
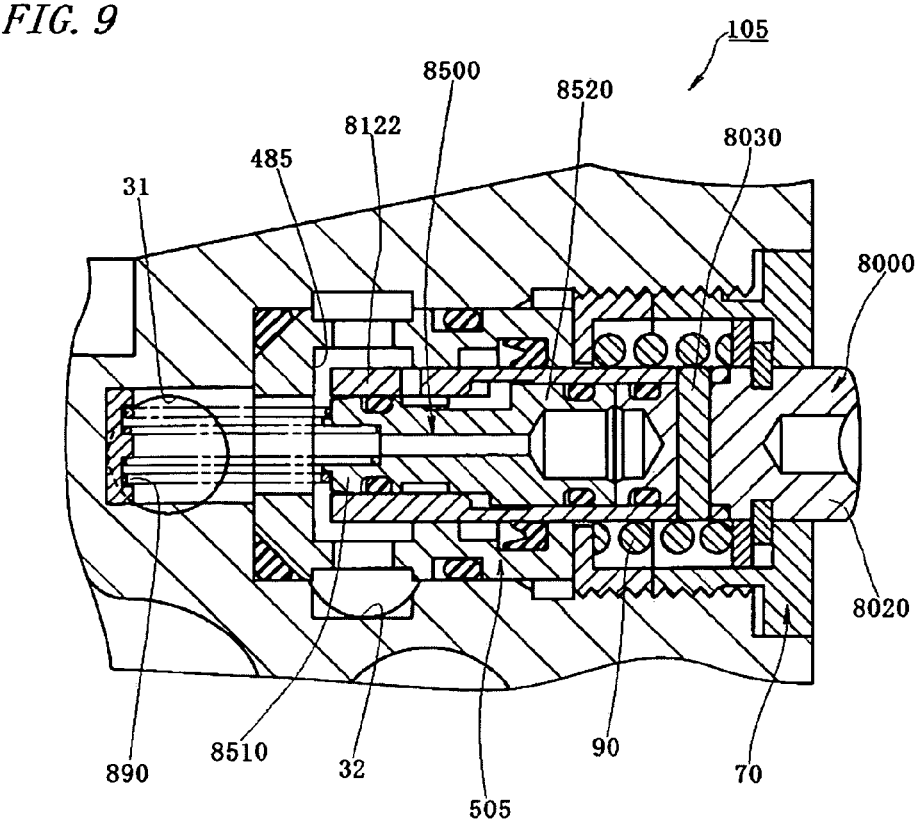
FIG. 9 is a sectional view showing a fully open state of the fifth embodiment of the selector valve according to the present invention.

FIGS. 7 through 9 are sectional views showing a fifth embodiment of a selector valve. The respective Figures show different states (FIG. 7 shows a fully closed state, FIG. 8 shows a half-open state and FIG. 9 shows a fully open state) of the selector valve. The features of the selector valve 105 of this fifth embodiment reside in that a holder 505 with a valve seat 485 obtained by integrally forming the holder 50 and the valve seat member 40 in the above-mentioned other embodiments is used and the valve element 80 is comprised of an outer piston 8000 and an inner piston 8500 movably fitted to an inner hole 8022 of the outer piston 8000. The outer piston 8000 has a divided structure composed of a front part 8010 fitted to the holder 505 and a rear part 8020 fitted to the cover ring 70. The divided two parts 8010, 8020 are integrated by a spring pin 8030. There are an enlarged-diameter hole part 8222 and a reduced-diameter hole part 8122 in the inner hole 8022 of the outer piston 8000. In accordance therewith, the inner piston 8500 includes an enlarged-diameter part 8520 fitted to the enlarged-diameter hole part 8222 and a reduced-diameter part 8510 fitted to the reduced-diameter hole part 8122. The enlarged-diameter part 8520 and the reduced-diameter part 8510 are provided at outer peripheries thereof with O-rings 8526, 8516, respectively, thereby sealing the area with respect to the inner hole 8022 side of the outer piston 8000. The inner piston 8500 having the stepped structure is further provided with a center through-hole 850 axially passing through the center thereof. Accordingly, the inner piston 8500 having the stepped structure is subjected to force (force for pushing the inner piston 8500 toward the depth of the cylinder hole 22) based on a difference in pressure receiving area between the enlarged-diameter part 8520 and the reduced-diameter part 8510 by pressure of the hydraulic liquid. The valve spring 90 as a main spring exerts a returning force to the outer piston 8000. Similarly, the secondary spring 890 having a smaller force than the valve spring 90 exerts a returning force to the reduced-diameter part 8510 of the inner piston 8500.

When the selector valve 105 is set to be in the normally open position, the returning force of the main spring 90 overcomes the pushing force (spring biasing force) generated by the spring of a link in a free state (though not shown, a spring force for pushing the link against the rear part 8020 of the outer piston is exerted) so that the outer piston 8000 is moved to the rear returning position. By this, the end of the front part 8010 of the outer piston 8000 is separated from the valve seat 485. In response to the operation of the outer piston 8000, the inner piston 8500 is in a position with the end of the enlarged-diameter part 8520 abutted with the inner wall of the rear part 8020 of the outer piston 8000 by the returning force of the secondary spring 890 and with the end of the reduced-diameter part on the front side brought away from the valve seat hole 4850. That is, the selector valve 105, when in its free state, maintains the fully open state shown in FIG. 9. In contrast, when the free state is changed to a state where a load is incurred to the knee, the link exerts a load pushing force (load pressure) to the outer piston 8000 in accordance with the change. The load pushing force overcomes the spring force of the primary spring 90 to make the end of the front part 8010 of the outer piston 8000 seat on the valve seat 485. A braking pressure is then generated on the first port 31 side. By this pressure, the force based on a difference in pressure receiving area overcomes the returning force of the secondary spring 890 to make the reduced-diameter part 8510 of the inner piston 8500 enter the valve seat hole 4850. By this, the selector valve 105 is brought into a fully closed state as shown in FIG. 7. Thereafter, when the load pushing force exerted to the outer piston 8000 is eliminated, the outer piston 8000 is returned to the open position by the returning force of the main spring 90. However, if a braking pressure is generated on the first port 31 side, the force based on a difference in pressure receiving area overcomes the returning force of the secondary spring 890 to maintain the state where the inner piston 8500 is pushed toward the valve seat 485 side. This state corresponds to the half-open state of the selector valve 105 shown in FIG. 8. In the half-open state, the inner piston 8500 (the front end part of the reduced-diameter part 8510) forms a restrictor between the front end part of the reduced-diameter part 8510 and the valve seat hole 4850 and the braking pressure is gradually released to the second port 32 side through the restrictor. As a result, the pressure on the first port 31 side is lowered. When the pressure is lowered to a predetermined value or less, the inner piston 8500 is brought away from the valve seat 485 side and returned to the inside of the outer piston 800 under the effect of the secondary spring 890.

Figure 10:
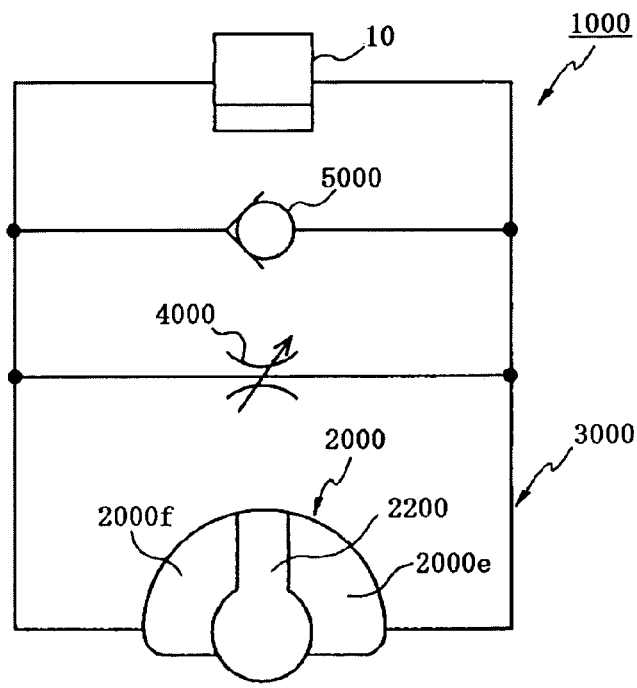
FIG. 10 is a circuit diagram showing one embodiment of a knee torque device according to the present invention.

FIG. 10 is a circuit diagram showing one embodiment of a knee torque device including a selector valve of the type mentioned above (for example, the selector valve 10). A chamber defining means 2000 in the knee torque device 1000 is a rotary type. Of two chambers 2000e, 2000f defined by the chamber defining means 2000, the first chamber 2000e is an extending chamber and the other second chamber 2000f is a flexing chamber. The extending chamber 2000e is a chamber into which a hydraulic liquid flows when the knee is extended and from which a hydraulic liquid flows out when the knee is bent. The two chambers 2000e, 2000f of the chamber defining means 2000 are communicated with each other through a path 3000, so that a hydraulic fluid can be flowed from one to the other or from the other to one. In order to flow the hydraulic liquid smoothly, the path 3000 may be provided with an accumulator.

The knee torque device 1000 includes a restrictor (i.e., a restricting valve) 4000 for generating a flow resistance in the path 3000 through which the two chambers 2000e, 2000f of the chamber defining means 2000 are communicated with each other, a check valve 5000 for prohibiting a flow from the first chamber 2000e toward the second chamber 2000f and allowing a flow in the reverse direction, and the selector valve 10 which is opened and closed by receiving a load of the wearer of an artificial leg. The restrictor 4000, the check valve 5000 and the selector valve 10 are connected to each other in parallel on the path 3000. As this restrictor 4000, various types can be applied. It is preferable to select one which is easy to adjust the amount of restriction. As a preferred example, there is a restrictor having an axially inclined cut-groove (for example, two cut-grooves spacedly arranged by 180 degrees in the peripheral direction) formed on the outer periphery of the valve element. It is possible for the restrictor 4000 to easily adjust the amount of restriction by screw adjustment in accordance with the body shape of the artificial leg wearer, the favorite walking style, etc. As the check valve 5000, a ball valve and a poppet valve can be applied.

Figure 11:
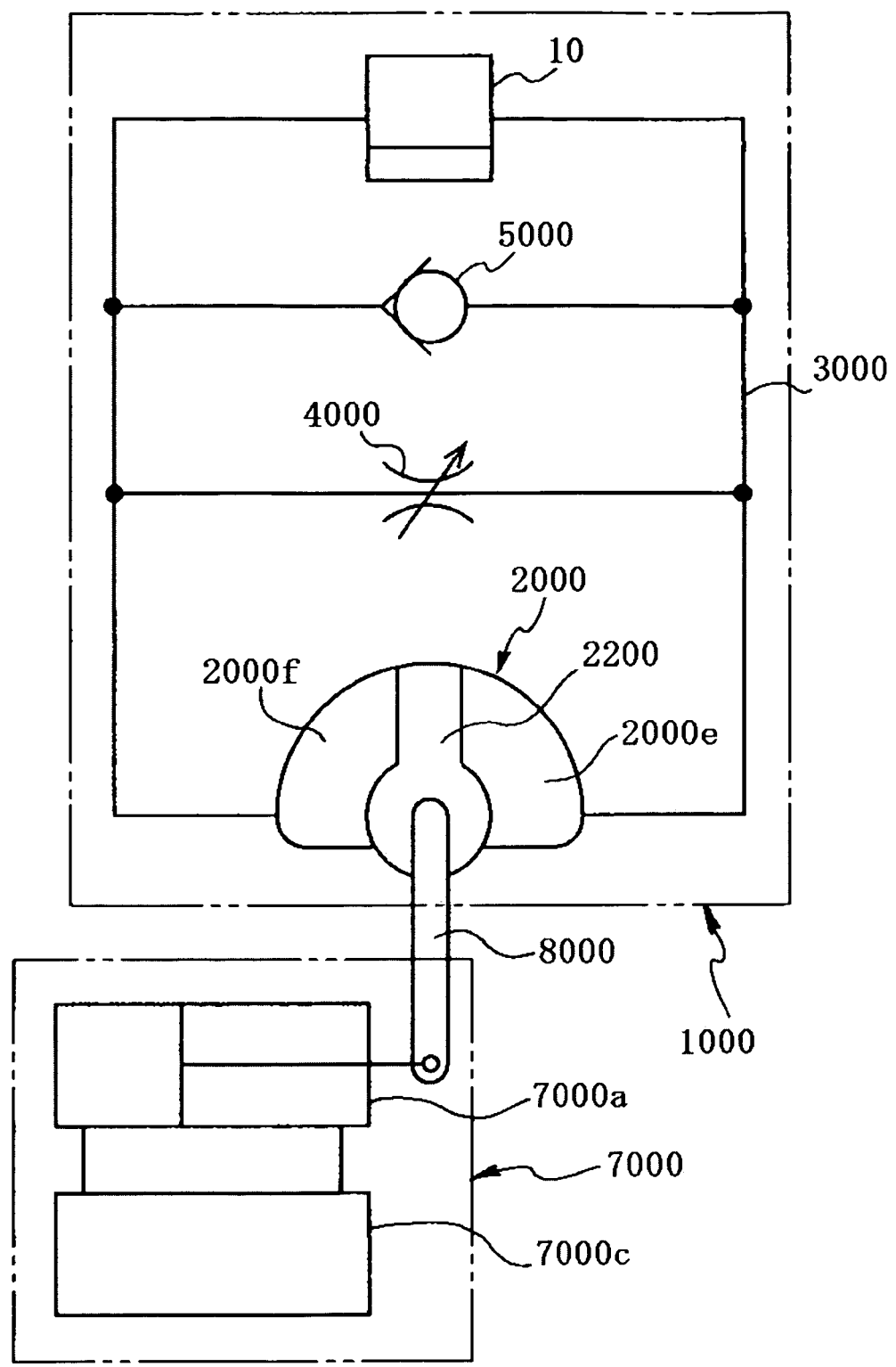
FIG. 11 is a circuit diagram of an artificial leg equipped with a pneumatic circuit in addition to the knee torque device of FIG. 10.

FIG. 11 shows a circuit in which an air cylinder device 7000 including an air cylinder 7000a and a pneumatic circuit 7000c is assembled with the knee torque device 1000 including the above-mentioned selector (for example, the selector valve 10). That is, the circuit is of the type where the stance phase of an artificial leg is controlled by the knee torque device 1000 and the swing phase of the same artificial leg is controlled by the air cylinder device 7000. As the air cylinder device 7000, a device known per se can be applied. In the air cylinder 7000a, two chambers are axially defined, one in the front and the other in the rear, by a piston within the cylinder. The pneumatic circuit 7000c includes a restrictor and a check valve and controls the flow of air flowing in and out of the front and rear chambers of the piston. The chamber defining means (i.e., the air cylinder 7000a) in the air cylinder device 7000 is of a piston type where a piston within the cylinder is axially reciprocally moved. In contrast, the chamber defining means 2000 in the knee torque device 1000 is of the rotary type where two chambers 2000c, 2000f are defined by the oscillating vane 2200. The knee torque device 1000 is constituted within a member which constitutes the knee. The oscillating vane 2200 on the knee torque device 1000 side and the piston 7000a on the air cylinder device 7000 side are connected to each other through a part (for example, a knee plate) 8000 of the artificial leg. The artificial leg comprising the assembling circuit of FIG. 11 obtains a flexible knee braking function in a stance phase from the knee torque device 1000 and a function for assisting the flexing and extending of the knee in a swing phase from the air cylinder device 7000.

Figure 12:
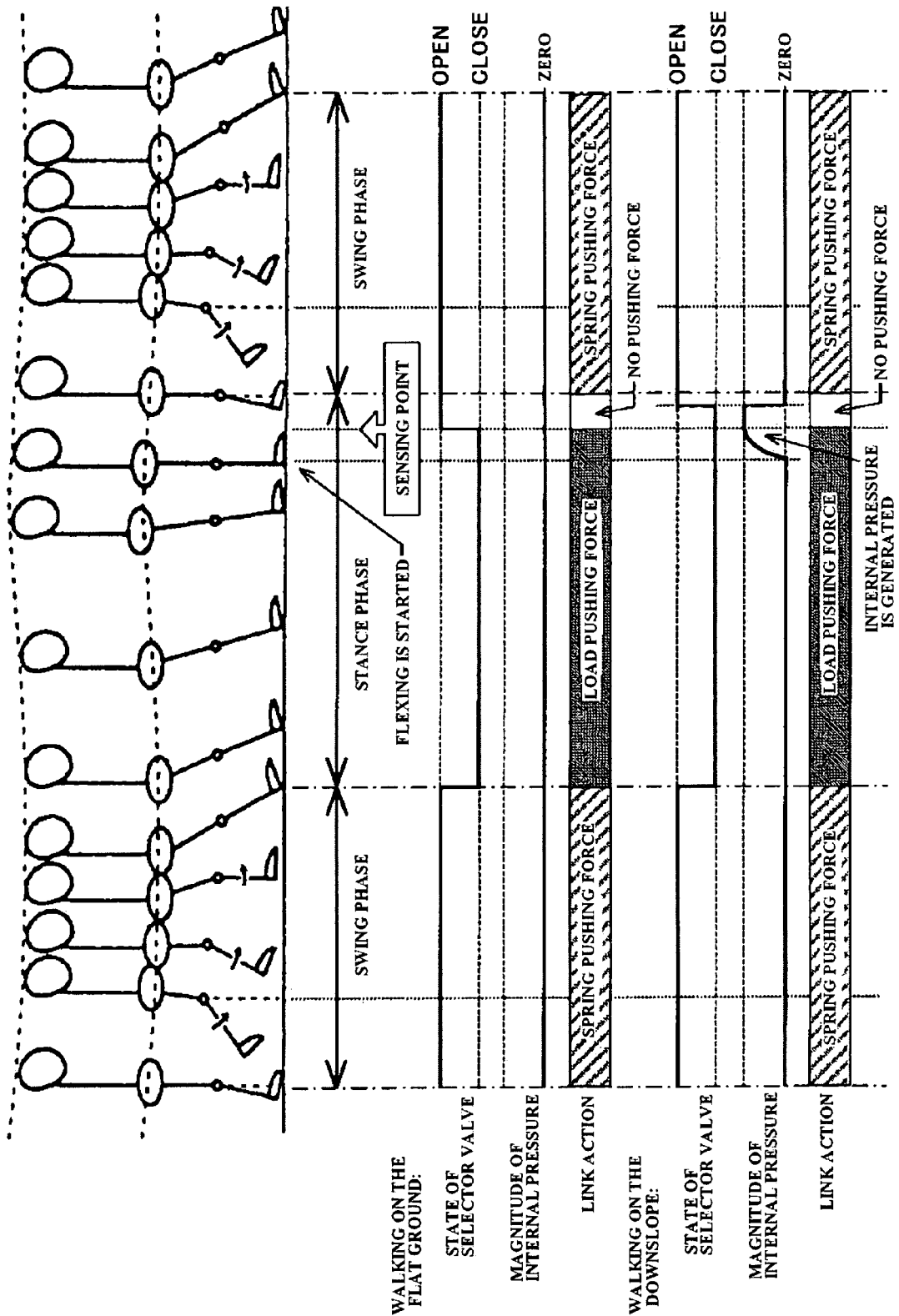
FIG. 12 is a view showing the switching timing of a normally-open type selector valve applicable to an artificial leg.
Figure 13:
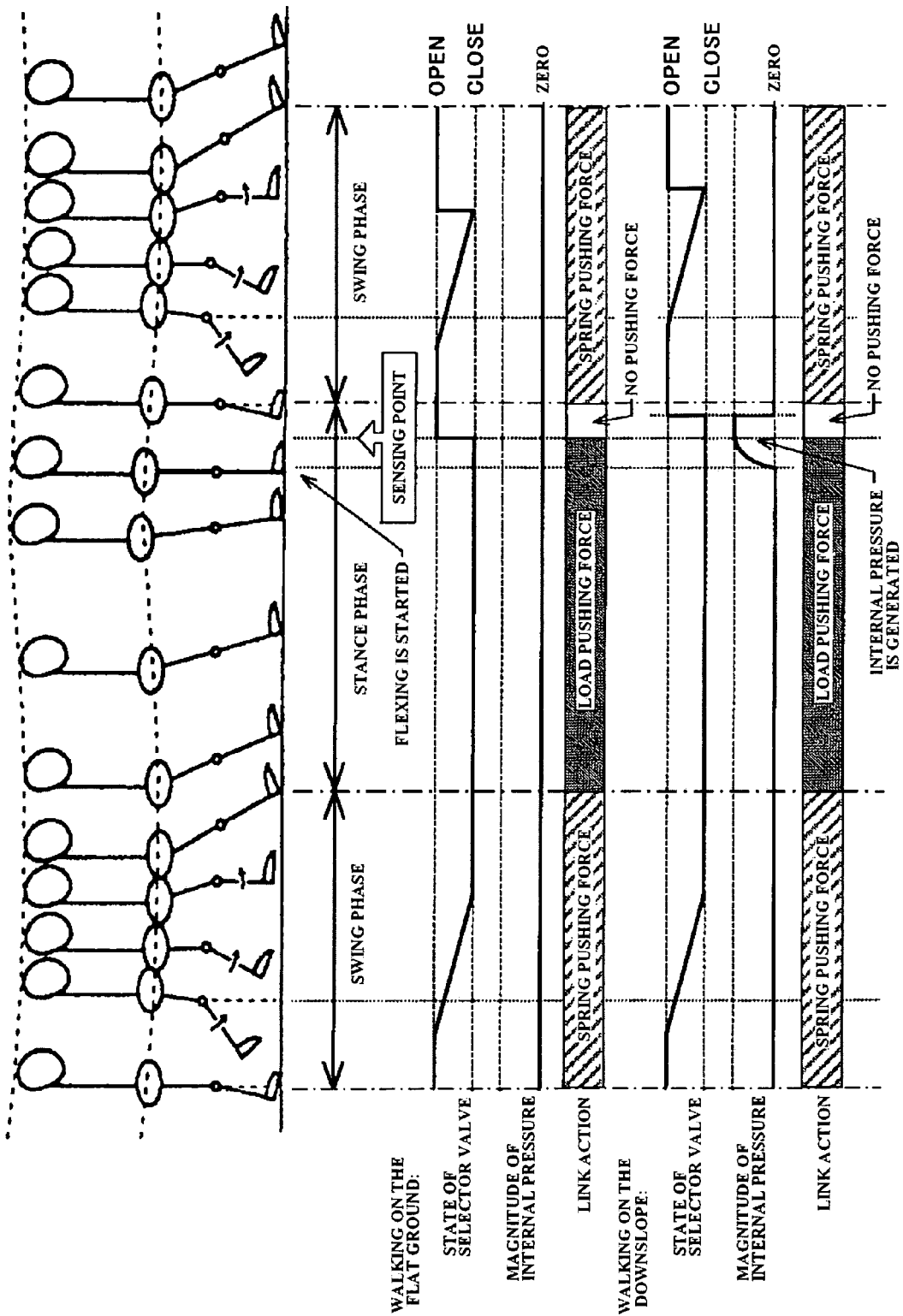
FIG. 13 is a view showing the switching timing of a normally-closed type selector valve applicable to an artificial leg.

FIGS. 12 and 13 are views showing examples of timing for switching a selector valve of a yielding artificial leg including a knee torque device, FIG. 12 is a normally open type and FIG. 13 is a normally closed type. In the selector valve according to the present invention, it will be understood that a braking pressure (internal pressure) against flexing of the knee is kept generated for a while (in the stage when the toe contacts the ground) even after the switching timing (i.e., sensing timing) of the selector valve.

The invention claimed is:

1. A selector valve comprising:
a housing having a cylinder hole;
a valve element capable of entering said cylinder hole of said housing and moving in an axial direction of said cylinder hole, a first end of said valve element entered in said cylinder hole being seated on/unseated from a valve seat on said housing side, said valve element receiving such an operating force in a second end on an opening side of said cylinder hole opposite to said first end as making said first end seat on said valve seat;
a valve spring for exerting a returning force for returning said valve element in an opposite direction of said operating force;
a first port located at the depth of said cylinder hole; and
a second port located near the opening of said cylinder hole from said first port,
said valve being opened and closed by making said first end of said valve element seat on/unseat from said valve seat according to the presence or absence of said operating force received in said second end of said valve element,
said selector valve capable of maintaining a closed position further including the following features,
(A) said valve element is formed in a stepped structure, and receives a force based on a difference in pressure receiving area by said stepped structure which results from the pressure of hydraulic fluid flowing through said first and second ports, and
(B) a seating state of said valve element seated on said valve seat is maintainable by force based on a difference in pressure receiving area by said stepped structure of said valve element when said first end of said valve element is seated on said valve seat on said housing side.

2. A selector valve according to claim 1, wherein said valve element includes an enlarged-diameter part on the side facing said first port and a reduced-diameter part near the opening of said cylinder hole, said valve element further including an internal path for communicating said reduced-diameter part of said first port and an outer periphery of said reduced-diameter part with each other through an inner peripheral part of the part seated on said valve seat.

3. A selector valve according to claim 1, wherein said valve element includes an outer piston having an inner hole along said axial direction and an inner piston fitted to the inner hole of said outer piston such that said inner piston is movable within the inner hole of said outer piston, and said valve spring includes a main spring for exerting a returning force to said outer piston and a secondary spring for exerting a returning force to said inner piston.

4. A knee torque device for exerting a resisting force to flexing of a knee, comprising a first chamber into which a hydraulic oil flows when the knee is extended, a second chamber into which a hydraulic oil flows when the knee is flexed, a path for communicating said second and first chambers with each other, a restrictor located between said first and second chambers on said path and adapted to exert a resisting force to flexing of the knee making good use of a flow resistance of said hydraulic oil passing through said restrictor, a check valve connected to said restrictor in parallel on said path and adapted to prevent a flow of said hydraulic oil from said first chamber to said second chamber but allow a flow in the opposite direction, and a selector valve connected to said check valve and said restrictor in parallel on said path and opened/closed by receiving a load of a wearer of said knee torque device, said selector valve including the following constructions and features,
(a) a housing having a cylinder hole;
(b) a valve element capable of entering said cylinder hole of said housing and moving in an axial direction of said cylinder hole, a first end of said valve element entered in said cylinder hole being seated on/unseated from a valve seat on said housing side, said valve element receiving such an operating force in a second end on an opening side of said cylinder hole opposite to said first end as making said first end seat on said valve seat;
(c) a valve spring for exerting a returning force for returning said valve element in an opposite direction of said operating force;
(d) a first port located at the depth of said cylinder hole;
(e) a second port located near the opening of said cylinder hole from said first port;
(f) said selector valve receiving an operating force at said second end of said valve element when said selector valve receives a load of a wearer of said knee torque device;
(g) said valve being opened and closed by making said first end of said valve element seat on/unseat from said valve seat according to the presence or absence of said operating force received in said second end of said valve element,
(A) said valve element being formed in a stepped structure, and receiving a force based on a difference in pressure receiving area by said stepped structure which results from the pressure of hydraulic fluid flowing through said first and second ports, and
(B) a seating state of said valve element seated on said valve seat being maintainable by force based on a difference in pressure receiving area by said stepped structure of said valve element when said first end of said valve element is seated on said valve seat on said housing side.

5. A knee torque device according to claim 4, wherein said force based on a difference in pressure receiving area is capable of maintaining a state where said valve element is made to seat on said valve seat by overcoming the returning force of said valve spring when the pressure on said first port side is a predetermined value or more.

6. A knee torque device according to claim 4, wherein said first and second chambers are divided by a vane pivotable about one point or a piston reciprocally movable in a linear direction.

7. A knee torque device according to claim 4, wherein said selector valve is of a normally closed type or a normally open type.

8. An artificial leg including a knee torque device of claim 4.

9. An artificial leg according to claim 8, wherein said knee torque device is such designed that a knee joint can be bent by an own load of a wearer of said artificial leg when said artificial leg is in a swing phase, and said artificial leg further includes an air cylinder device for assisting the flexing and extending of the knee in a swing phase.

* * * * *